United States Patent [19]

Adams

[11] 4,295,472
[45] Oct. 20, 1981

[54] HEART RATE MONITOR

[75] Inventor: John M. Adams, Mesa, Ariz.

[73] Assignee: Medtronic, Inc., Minneapolis, Minn.

[21] Appl. No.: 80,597

[22] Filed: Oct. 1, 1979

Related U.S. Application Data

[63] Continuation of Ser. No. 851,030, Nov. 14, 1977, abandoned, which is a continuation of Ser. No. 714,873, Aug. 16, 1976, abandoned.

[51] Int. Cl.³ .............................................. A61N 5/04
[52] U.S. Cl. ................................... 128/690; 128/706
[58] Field of Search ............... 128/690, 706, 710, 642, 128/734, 689

[56] References Cited

U.S. PATENT DOCUMENTS

| | | | |
|---|---|---|---|
| 3,144,018 | 8/1964 | Head | 128/642 |
| 3,870,034 | 5/1975 | James | 128/734 |
| 4,009,708 | 3/1977 | Fay, Jr. | 128/690 |
| 4,091,610 | 5/1978 | Sasaki et al. | 128/690 |
| 4,120,294 | 10/1978 | Wolfe | 128/710 |

Primary Examiner—William E. Kamm
Attorney, Agent, or Firm—Carl A. Forest; Lew Schwartz; Joseph F. Breimayer

[57] ABSTRACT

A wrist watch size heart rate monitor coupled with a flexible metal expansion band detects a electrocardiac signal on one arm and applies that detected signal to electronic circuitry within the monitor. Means are also included for receiving a second electrocardiac signal from the other arm to obtain an electrocardiac lead I signal. The receiving means may be a contact member adapted to being placed in physical contact with a second flexible metal expansion band around the wrist of the other arm and having a like contact member associated therewith or the receiving means may be metal members adapted to having the thumb and a finger of the hand of the other arm squeezed thereagainst.

4 Claims, 6 Drawing Figures

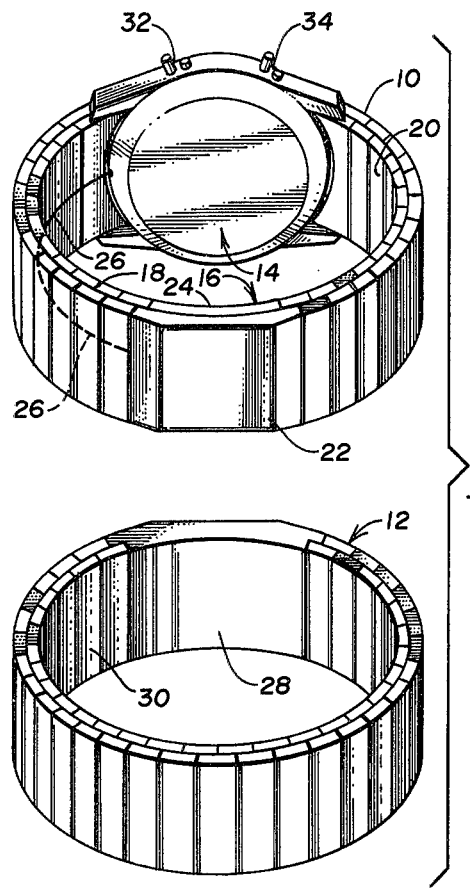
*Fig.1*
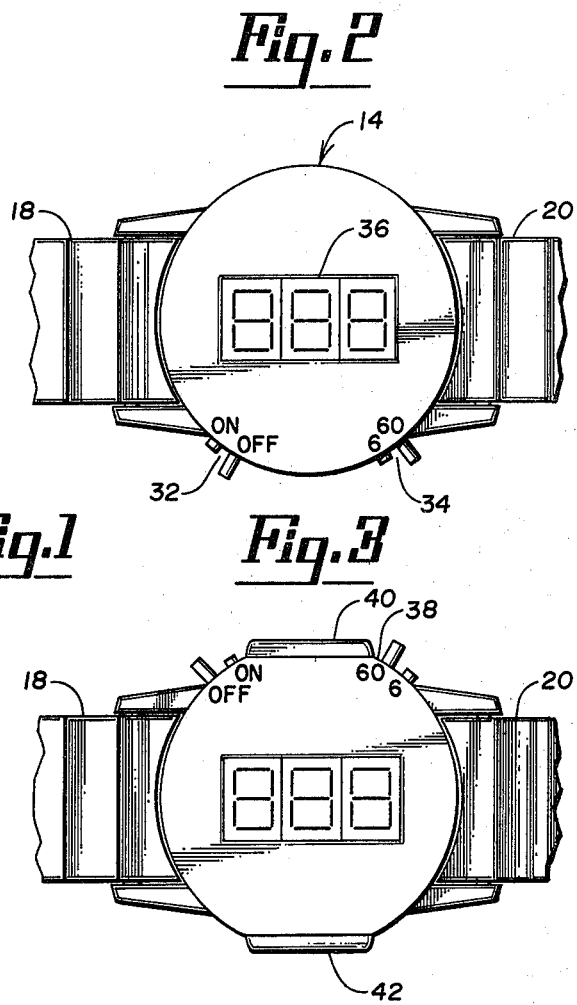
*Fig.2*
*Fig.3*
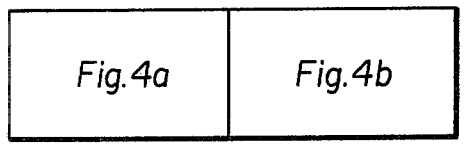
*Fig.4*
| Fig.4a | Fig.4b |

HEART RATE MONITOR

This is a continuation of application Ser. No. 851,030 filed Nov. 14, 1977, now abandoned which was itself a continuation of application Ser. No. 714,873 filed Aug. 16, 1976, abandoned.

This invention relates to cardiac monitoring and more particularly to apparatus for detecting and providing cardiac signals to processing circuitry.

In the prior art, many devices exist which are adapted to be used in measuring the heart rate of a subject. The devices vary from sophisticated, computer-controlled apparatus capable of monitoring a plurality of patients simultaneously to small, individual patient units designed to monitor only the heart rate. Of these latter type devices, the majority accomplish the task of measuring the heart rate by measuring the pulse rate and are implemented in the form of a wrist band with pressure sensitive or sound sensitive transducers affixed to the band and positioned on the wrist adjacent to the palm of the hand.

In addition to the pulse monitoring devices, some small individual devices measure the electrocardiac signal which may be detected from the skin of the subject. This has been done by wires running from the device to electrodes affixed by conventional means to the chest area of the subject. In this manner, a conventional electrocardiac signal is detected by the electrodes and applied through the wires to the device. The device may be adapted for use by the subject at several different places of the body. For instance, the device may include a small box-like configuration adapted to be worn on the belt of the subject or the device may be in the form of a wrist band adapted for being worn around the wrist. A problem, however, is that the wires leading from the chest area to the device, wherever it may be placed, are prone to disconnection and breakage as the subject moves, thereby terminating the ability of the device to monitor.

The reason that wires have been utilized in measuring the electrocardiac activity in the past is that it has been thought that it is necessary to continuously monitor the patient. However, in many instances, it is only necessary to take an instantaneous reading of the heart rate. For instance, if a subject has previously suffered a coronary attack and has recovered sufficiently to lead a normal, or near normal, life with the exception that his heart rate should be limited to a certain maximum, it would only be necessary to take a measurement of the heart rate during strenuous activity, such as exercising. In this case, a continual monitoring of the cardiac activity of that subject's heart would be wasteful utilization of the power source (battery) powering the device. Of course the prior art apparatus could be modified by placing a simple switch on the device to render it active only when desired by the subject. However, the problem of wires running from the patient's chest area to the area where the device is located, still remains.

In accordance with one preferred embodiment of this invention, there is provided a cardiac signal detecter including a housing containing circuitry for processing a pair of electric signals, each one of which manifests the electric signal at a different limb of a person, and further including a band member of an electrically conductive material selected to be capable of detecting electric signals on the skin of such person, said band being affixed to said housing and of a size to allow the housing and band combination to firmly contact one of the limbs. The band is in electric communication with the circuitry to provide the signal at said one limb as one of the pair of signals. In addition, there is provided receiving means mechanically fixed to the housing and band combination and electrically isolated therefrom. The receiving means is in electrical communication with the circuitry and adapted to receive, by contact, an electric signal from the other limb and to provide such received signal to the circuitry as the other one of the pair of signals.

A preferred embodiment of this invention is hereafter described with specific reference being made to the following FIGS., in which:

FIG. 1 shows a pair of wrist band detectors adapted for use with circuitry associated with one of the wrist bands;

FIG. 2 shows the face of the housing containing the circuitry for processing the signals detected by the detectors of FIG. 1;

FIG. 3 shows an alternate embodiment of the housing containing the circuitry shown in FIG. 1.

Figure 4A:
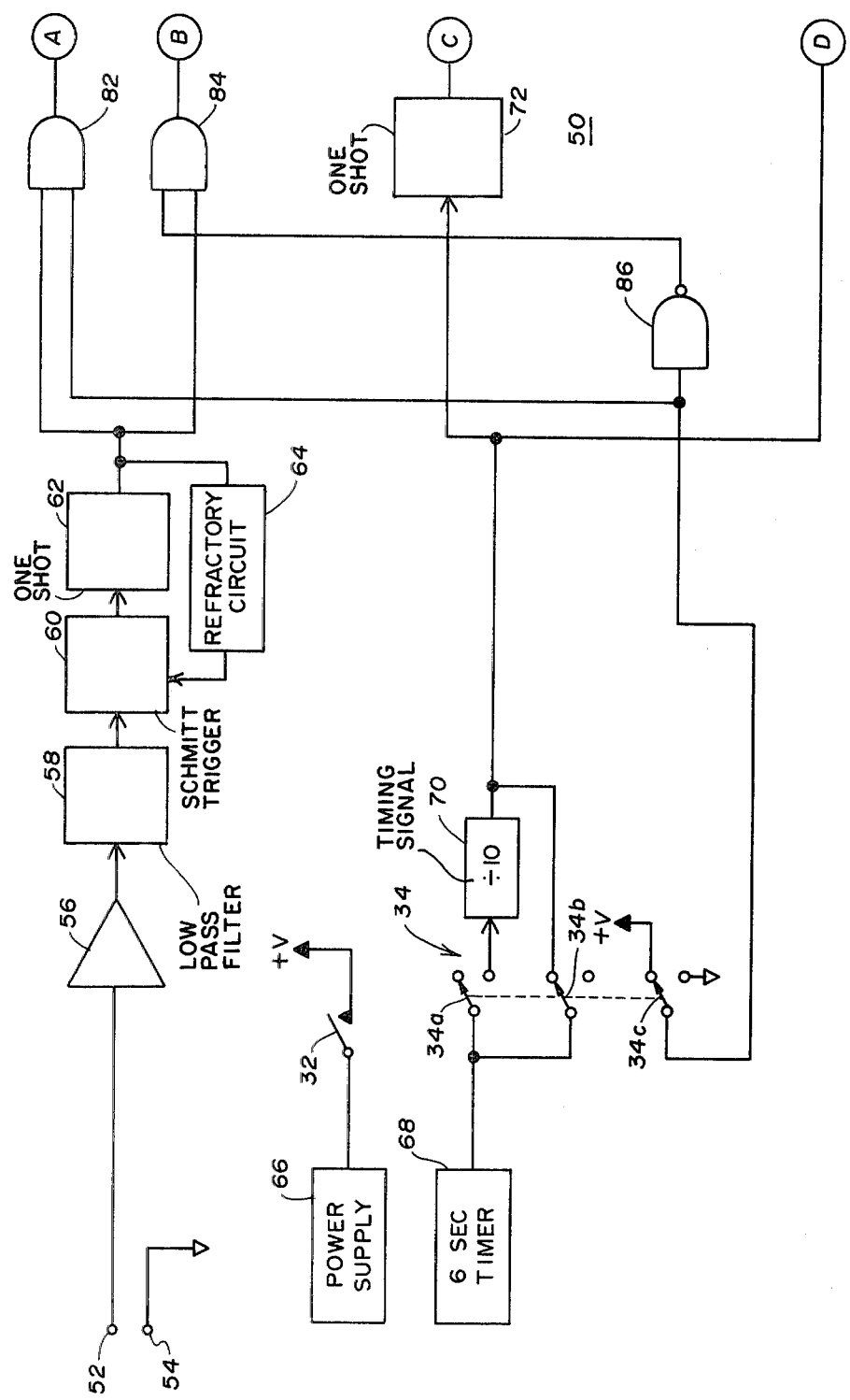
FIG. 4 shows the orientation of FIGS. 4a and 4b which in turn show, in block format, a circuit diagram for processing the signals detected by the apparatus shown in FIG. 1 or FIG. 3.

Referring now to FIG. 1, a pair of wrist bands 10 and 12 each adapted to be worn on a different wrist of a subject are shown. Wrist band 10 includes the housing 14, a contact member 16 and a pair of flexible metal expansion members 18 and 20, connecting housing 14 contact 16.

Figure 4B:
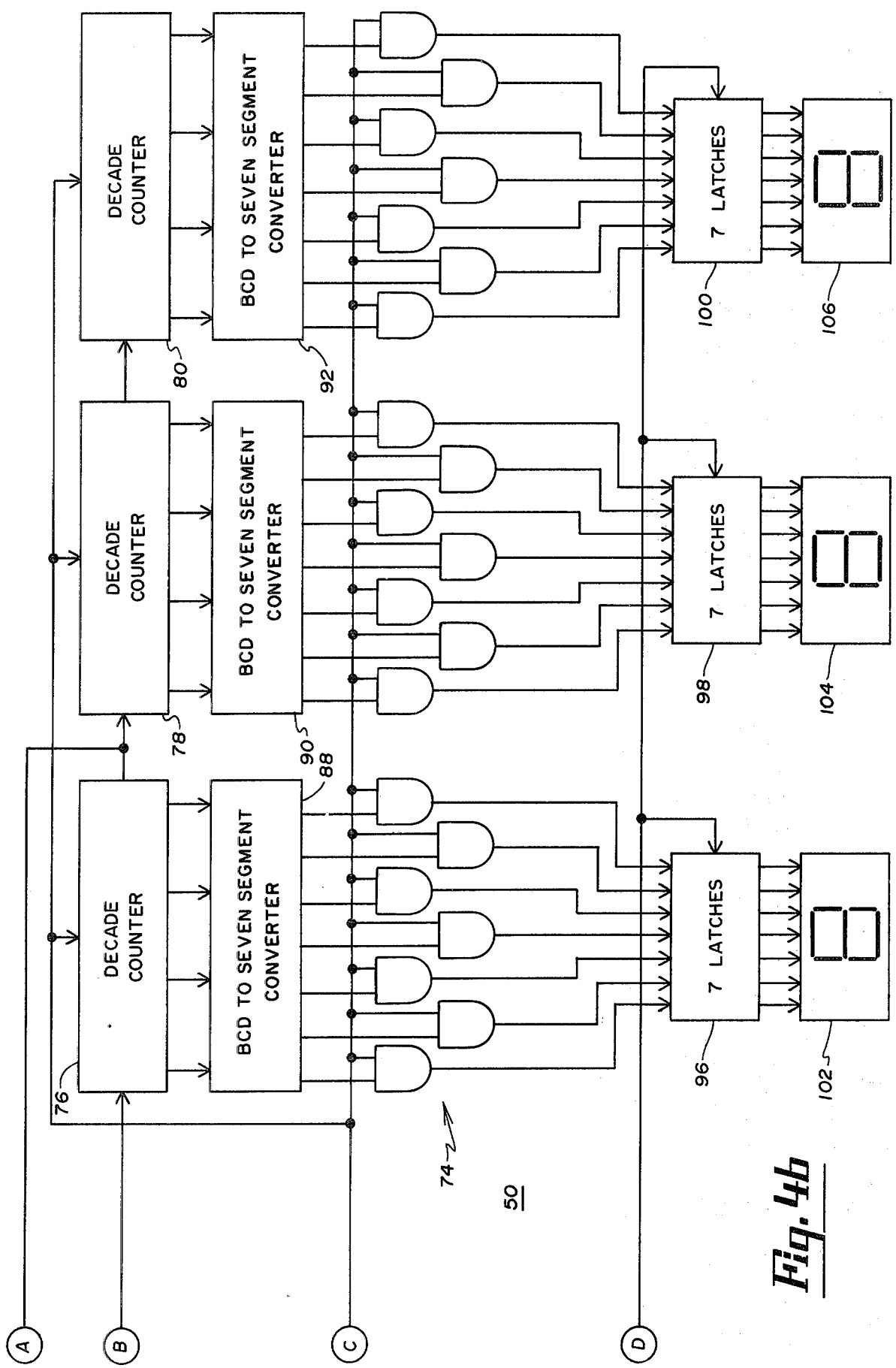

Housing 14 contains the electronic circuitry used in processing the pair of signals representing a lead I electrocardiac lead signal. This circuitry will be described in detail hereafter with respect to FIGS. 4a and 4b, arranged as shown in FIG. 4. As is wellknown in the art, a lead I electrocardiac signal is derived from the left and right hand wrists of the subject and measures the electrical activity of the heart along a plane running generally parallel to the ground as a patient is in an upright position.

Contact member 16 includes a conductive portion 22 and an insulator portion 24 arranged so that conductive portion 22 is not in electrical communication with expansion members 18 or 20. A wire 26 or other electrical conducting member connects conductive portion 22 to the circuitry within housing 14.

Expansion members 18 and 20 may be similar to conventional metal expansion watch bands. However, members 18 and 20 should be of a material capable of detecting electrical signals appearing on the skin when in firm contact with the skin. In addition, members 18 and 20 should be constructed to conduct the detected electric signal to the electric circuitry within housing 14, with which circuitry members 18 and 20 are in electrical communication. Expansion members 18 and 20 should also be constructed to be adjustable by either deleting or adding links therein so that the entire wrist band 10 can be sized to fit firmly around the wrist of the subject thereby allowing a firm contact between bands 18 and 20 and the skin to achieve good electrical detection of the skin signals. Further, bands 18 and 20 should be of an adequate width to allow sufficient surface area for good contact.

Band 12 is similar to band 10 with the exception that no housing for electrical circuitry is included and no insulator portion, such as portion 24, is included in contact member 28. More specifically, band 12 consists of conductive contact member 28 and a flexible metal expansion member 30 of similar design to members 18 and 20. If desired, member 30 may be divided in half and a conventional wrist watch can be inserted in a manner similar to the inclusion of housing 14 in band 10.

Band 12 is adapted to be worn on the wrist opposite of band 10. When it is desired to take the subject's heart rate, contact member 28 is placed in firm contact with contact member 16. In this manner, the electrocardiac skin signal detected by expansion member 30 from the wrist upon which band 12 is worn are applied electrically through contact member 28 to the conductive portion 22 of contact member 16. From portion 22, the electrical signal is applied through wire 26 to the electronic circuitry in housing 14. At the same time, the signal from the other wrist is detected by expansion members 18 and 20 and applied directly to the electric circuitry within housing 14.

At this point it should be noted that the exposed surface areas of contact members 16 and 28 are designed to provide a good electrical connection when physically placed in contact with one another. Such design may include similar size and a mirror image non-flat surfaces.

Housing 14 also includes a pair of switches 32 and 34. Each of switches 32 and 34 includes a pair of pushbuttons, one of which will always extend out further than the other. To cause either one of switches 32 or 34 to change states, it is necessary to depress the more exposed button thereof. Switch 32 is an ON/OFF switch which should only be in the On state when measuring the heart rate and switch 34 is a 6/60 second selector switch, that is, the rate can be selectively measured by counting R-waves for six seconds and reporting ten times that count as beats per minute or the rate can be measured by counting R-waves for sixty seconds and reporting that count directly as beats per minute. Both switches 32 and 34 affect the electronic circuitry within housing 14 in the manner described with respect to FIG. 4a.

With respect to ON/OFF switch 32, it should be noted that a pressure sensitive switch in contact member 16 of FIG. 1 or contacts 40 and 42 of FIG. 3 could serve the same function with the advantage that the subject would not forget to turn the unit on or off.

Referring now to FIG. 2, the face of housing 14 is shown and includes a three-digit display 36 with each digit consisting of seven illuminable segments. Selected ones of each of the segments can be illuminated to cause any of the digits 0-9 to be displayed in each digit of display 36. Display 36 may be any conventional digital display.

Referring now to FIG. 3, a face plate 38 is shown which constitutes an alternate embodiment to the apparatus shown in FIG. 1. The only difference between housing 38 shown in FIG. 3 and housing 14 shown in FIGS. 1 and 2 is the addition of contact members 40 and 42. Members 40 and 42 are positioned on the periphery of housing 38 in a position approximately 90 degrees from the axis through the flexible members 18 and 20. In utilizing housing 38, the second watch band 12 apparatus shown in FIG. 1 is eliminated. Rather, the thumb and one of the fingers of the hand remote from the limb wearing the monitoring apparatus are placed firmly in contact with contact members 40 and 42. In this manner, the electrocardiac signal present on the skin at the fingertips is transmitted through members 40 and 42 to the circuitry within housing 38. A word of caution with regard to the utilization the embodiment shown in FIG. 3 is that some individuals may have calloused fingertips that could prevent adequate signal transmission from the skin to contacts 40 and 42.

Referring now to FIGS. 4a and b, arranged as shown in FIG. 4, a block diagram of the circuitry 50 contained within housing 14 is shown. The two signals from the wrists of the subject wearing the apparatus of either FIG. 1 or FIG. 3 are applied respectively to terminals 52 and 54. Terminal 54 is connected to a point of reference potential, such as system ground and terminal 52 is connected to the amplifying input of amplifier 56. The amplified signal from amplifier 56 is passed through a low-pass filter, which may filter out all signals having a frequency above, for instance, 20 hertz to thereby eliminate 60 cycle and muscle noise.

The output of low-pass filter 58 is connected to the input of a voltage threshold sensitive circuit 60, such as a Schmitt trigger. Circuit 60 provides a pulse signal each time the voltage applied thereto exceeds the set threshold voltage there. The threshold voltage of circuit 60 is adjusted to be responsive only to the R-wave of the electrocardiac signal so as to provide a pulse each time an R-wave occurs. It should be noted that the R-wave of an electrocardiac signal is a positive excursion of the signal to a point of maximum amplitude of the signal. The R-wave is normally proceeded by a smaller magnitude positive excursion known as the P-wave and followed by another smaller magnitude positive excursion known as the T-wave. Although not shown in the Figures herein, a potentiometer adjustment to Schmitt trigger 60 may be provided on housing 14 to allow the threshold magnitude to be adjusted so that Schmitt trigger 60 is only triggered by the R-wave and not the P- or T-waves for the individual patient utilizing the rate monitoring apparatus.

The output pulse from Schmitt trigger 60 is provided to a "one-shot", or monostable multivibrator, 62, which provides a controlled pulse signal each time an R-wave is detected by Schmitt trigger 60. The output from "one-shot" 62 is provided through a refractory circuit 64 back to an inhibit input of Schmitt trigger 60. Refractory circuit 64 may be simply another "one-shot" circuit which inhibits Schmitt trigger 60 from providing another pulse for a certain time (e.g., the width of the pulse provided therefrom) after the detection of the initial R-wave. Refractory circuit 64 is provided to prevent a large magnitude T-wave from being detected as a second R-wave or, on the other hand, in the event that a P-wave is detected as an R-wave, refractory circuit 64 prevents the R-wave shortly following the P-wave from being detected as a second R-wave. Again, a potentiometer adjustment (not shown) may be incorporated in housing 14 to allow the refractory time to be adjusted, depending upon the patient's normal heart rate and the maximum rate to which the patient's heart should be allowed to be.

The signal processing circuitry consisting of amplifier 56, filter 58, Schmitt trigger 60, one-shot 62 and refractory circuit 64 is all under the operability control of power supply 66. For clarity, the application of power +V to each of these components is not shown. However, it should be understood that this is the case as well as power being supplied to each of the other components described with respect to the block diagram shown in FIG. 4. As previously mentioned, the output from power supply 66 is under the control of switch 32 such that when switch 32 is closed power +V can be applied. However, when switch 32 is open, the power to each of the components in circuit 50 is cut off and thus the components are non-operative.

The output from one-shot 62 is a pulse substantially coincident in time with each R-wave of the electrocardiac signal. This pulse is processed by the remainder of the logic circuitry in the manner hereafter described.

The heart of the logic circuitry is the six second timer 68 which provides a pulse every six seconds. 6/60 switch 34 actually is a three-bank switch consisting of switches 34a, 34b and 34c with each switch having a switching arm and a pair of output poles shown schematically in the upper or lower positions in which the switch arm may be placed in. The switch arms of switches 34a and 34b are both connected to the output of the six second timer 68. The upper contact of switch 34a and the lower contact of switch 34b are both disconnected from any other component within the system. The lower contact of switch 34a is connected to a conventional divide by 10 circuit which provides an output pulse after ten input pulses have been provided thereto, or, in the case of circuit 50, every sixty seconds. The upper terminal of switch 34b is connected to the output of the divide by ten circuit 70. Thus, when switch 34 is in the "up" position, divide by ten circuit 70 is bypassed and, a pulse appears at the output of divide by ten circuit 70 every six seconds and when switch 34 is in the "down" position, a pulse appears at the output of divide by ten circuit 70 every sixty seconds.

The upper terminal of switch 34c is connected to +V voltage which herein is equivalent to a logic "1" signal. Connected to the lower terminal of switch 34c is reference, or ground, voltage which herein is equivalent to a logic "0" signal.

The timing pulse from the output of divide by ten circuit 70, when switch 34 is in the "down" position or from the upper terminal of switch 34b when switch 34 is in the "up" position, is provided as the input to one-shot circuit 72 to cause a desired width pulse to be provided therefrom. The output pulse from one-shot 72 is provided to the enable input to each of twenty-one AND gates 74, which are divided into three groups of seven gates each. The output from one-shot 72 is also connected to the reset input of each of three decade counters 76, 78, and 80, with the counter 76 constituting the least significant digit and counter 80 constituting the most significant digit. Counters 76, 78 and 80 are designed to respond to the trailing edge of the pulse from one-shot 72 to be reset to a count of zero upon its occurrance.

When switch 34c is in the "up" position, +V voltage is applied to the enabled input of AND gate 82 so that the pulses corresponding to the detected R-waves of the electrocardiac signal appearing at the output of one-shot 62 are applied through AND gate 82 to the input of decade counter 78. When switch 34c is in the "down" position, ground voltage is applied through inverter 86, and from there as a +V voltage, or logic "1" signal, to the enable input of AND gate 84, so that the pulses corresponding to the detected R-waves are applied through AND gate 84 to the input of decade counter 76.

The four outputs from each stage of the decade counters 76, 78, and 80 are respectively applied to four-bit to seven-segment convertor circuits 88, 90, and 92 which convert a four line binary coded decimal (BCD) signal from counters 76, 78, or 80 to an appropriate seven line signal which will cause a seven segment display to display the value of the BCD signal. Each of the seven outputs from each of the convertor circuits 88, 90, and 92 are applied through the associated AND gate 74 at the time the gate is enabled by the pulse from one-shot 72, to a latch circuit, represented in the block diagram as one of the latches in the seven latch circuits 96, 98, and 100. In addition, the pulse signal from the output of divide by ten circuit 70 or the upper terminal of switch 34b is applied to the reset input of each latch in latch circuits 96, 98, and 100. The output signals from each of the latches 96, 98, and 100 are applied respectively to seven-segment display devices 102, 104, and 106.

The operation of circuit 50 will hereinafter be described. First, assuming that switch 34 is in the "up" or six second position, as shown in FIG. 4a, a pulse will be provided to trigger one-shot 72 every six seconds. Coincident with each latch in latch circuits 96, 98, and 100 is reset and after one-shot 72 is triggered, decade counters 76, 78, and 80 are reset at the trailing edge of the one-shot 72 pulse. When switch 34 is in the "up" position, a +V voltage, or logic "1", is applied to the enable input of AND gate 82 and a negative voltage, or logic "0", is applied through inverter 86 to the enable input of AND gate 84. Thus, AND gate 82 is enabled and passes the detected R-wave pulses from one-shot 62 to the second stage decade counter 78. Each time a pulse is applied to decade counter 78 it is incremented by one. After six seconds, a pulse is applied to clear the latches in latch circuits 96, 98, and 100 and to cause a pulse to be provided from one-shot 72. This pulse enables each of the AND gates 74 to provide the signals stored by counters 76, 78, and 80, as converted by convertors 88, 90, and 92, to latches 96, 98, and 100. It should be noted that with switch arm 34c in the "up" position, the least significant stage decade counter 76 is bypassed and thus maintains a zero count therein. In this situation, the seven latches in latches 96 are set to cause display 102 to display a numerical zero as the least significant digit of the display 36, whereby the rate displayed is ten times the number of pulses counted during the six second interval. Thus, if six pulses had been provided from one-shot 62 during the six second interval, display 104 would have a six appearing thereon and displays 102 and 106 would each have a zero displayed thereon or in other words, a heart rate of 60 would be displayed. On the other hand, if twelve pulses had been counted during the six second interval, decade counter 78 would contain a two and decade counter 80 a one count. There would be applied through in the manner previously described to displays 104 and 106 with display 102 being zero, whereby a count of 120 would be displayed.

The trailing edge of the pulse from one-shot 72 would then reset each of the counters 76, 78, and 80 and the above process would be repeated again until such time as another pulse appeared at the input of one-shot 72 which pulse would clear the latches in latch circuits 96, 98, and 100 and cause one-shot 72 to provide a pulse to enable gate 74.

When switch 34 is placed in the "down" position, or sixty second position, it requires ten pulses from the six second timer 68 to be applied through divide by ten circuit 70 before a pulse is applied to one-shot 72. Between one-shot 72 pulses, pulses provided at the output of one-shot 62 are applied through enabled AND gate 84 to decade counter 76. In this instance, ground voltage from switch 34c is inverted by invertor 86 and then applied to enable AND gate 84, whereby least significant counter 76 is not bypassed and the count therein is displayed on display 102 in the manner previously described.

What is claimed is:

1. A cardiac signal detector comprising:
a housing containing circuitry for detecting and counting individual heartbeats of a person as said heartbeats are manifested by a pair of electric signals, each one of which signals manifests the electrocardiac potential at a different limb of said person, said circuitry including means for selecting the time during which said detected beats are counted to be six or sixty seconds;
a band member of an electrically conductive material selected to be capable of detecting electric signals on the skin of such person, said band being affixed to said housing and said housing and band combination being capable of firmly contacting one of said limbs, said band and housing combination further being in electric communication with said circuitry to provide the signal at said one limb as one of said pair of signals;
receiving means electrically isolated from said housing and band combination, said receiving means being adapted for physical contact with said other limb and being in electrical communication with said circuitry to provide the other one of said pair of signals;
display means for providing a signal representative of the heart rate of said person;
timing means responsive to the state of said means for selecting for providing timing signals to cause said detecting beats to be counted for said selected time;
means responsive to said timing signals and the counted beats for providing signals representative of the heart rate of said person to said display means;
means responsive to said means for selecting whereby in the event a sixty second timing signal is selected, said display means displays the number of detected and counted heartbeats;
and
decade means responsive to said means for selecting whereby in the event a six second timing signal is selected, said display means displays ten times the number of detected and counted heartbeats.

2. The invention according to claim 1 wherein said decade means comprises means for applying the count of said detecting and counting means to the "10's" and higher significant digits of said display.

3. A cardiac signal detector comprising:
a housing containing circuitry for sensing a pair of electric signals, each one of which manifests the electric signal at a different limb of a person;
a first band member of an electrically conductive material selected to be capable of detecting electric signals on the skin of such person, said first band being affixed to said housing and said housing and first band combination being capable of firmly contacting one of said limbs, said first band and housing combination further being in electric communication with said circuitry to provide the signal at said one limb as one of said pair of signals;
a second band member of electrically conductive material selected to be capable of detecting electric signals on the skin of said person and adapted to firmly contact the other one of said pair of limbs; and
a contact plate carried by said first band and housing combination and electrically isolated therefrom, said contact plate further being adapted for physical contact with said second band member and in electrical communication with said circuitry to provide the other one of said pair of signals.

4. The invention according to claim 3 wherein said contact plate is carried by said first band member.

* * * * *